(12) United States Patent
Boretius et al.

(10) Patent No.: US 11,478,635 B2
(45) Date of Patent: Oct. 25, 2022

(54) IMPLANT IN THE FORM OF A WOUND CUFF ELECTRODE ASSEMBLY

(71) Applicant: Neuroloop GmbH, Freiburg (DE)

(72) Inventors: Tim Boretius, Freiburg (DE); Dennis Plachta, Freiburg (DE); Fabian Kimmig, Freiburg (DE)

(73) Assignee: NEUROLOOP GMBH, Freiburg (DE)

( * ) Notice: Subject to any disclaimer, the term of this patent is extended or adjusted under 35 U.S.C. 154(b) by 142 days.

(21) Appl. No.: 16/981,604

(22) PCT Filed: Feb. 26, 2019

(86) PCT No.: PCT/EP2019/054643
§ 371 (c)(1),
(2) Date: Sep. 16, 2020

(87) PCT Pub. No.: WO2019/174900
PCT Pub. Date: Sep. 19, 2019

(65) Prior Publication Data
US 2021/0016081 A1 Jan. 21, 2021

(30) Foreign Application Priority Data
Mar. 16, 2018 (DE) .................... 10 2018 204 036.2

(51) Int. Cl.
*A61N 1/05* (2006.01)
*A61N 1/375* (2006.01)
*A61N 1/36* (2006.01)

(52) U.S. Cl.
CPC ....... *A61N 1/0556* (2013.01); *A61N 1/37518* (2017.08); *A61N 1/3605* (2013.01)

(58) Field of Classification Search
None
See application file for complete search history.

(56) References Cited

U.S. PATENT DOCUMENTS

| 5,919,220 A | 7/1999 | Stieglitz et al. |
| 7,809,442 B2 * | 10/2010 | Bolea ................. A61N 1/37229 607/42 |
| 2004/0015204 A1 | 1/2004 | Whitehurst et al. |
| 2006/0030919 A1 | 2/2006 | Mrva et al. |

(Continued)

FOREIGN PATENT DOCUMENTS

| DE | 44 33 111 A1 | 3/1996 |
| WO | 2016/055512 A1 | 4/2016 |

OTHER PUBLICATIONS

International Search Report for PCT/EP2019/054643, dated Jun. 14, 2019; English translation submitted herewith (6 pgs.).

(Continued)

*Primary Examiner* — Michael W Kahelin
*Assistant Examiner* — Elizabeth K So
(74) *Attorney, Agent, or Firm* — Fitch, Even, Tabin & Flannery LLP

(57) ABSTRACT

The invention has a contact assembly including a spatial longitudinal extension which is orientated parallel to the winding axis. The contact assembly is fixedly joined to the carrier substrate along a joining region which has a joining region length orientated in parallel to the winding axis. The orthogonal projection relative to the winding axis overlaps with a first region of the carrier substrate which is wound into a tube.

16 Claims, 1 Drawing Sheet

(56) References Cited

U.S. PATENT DOCUMENTS

2015/0374296 A1   12/2015  Baru et al.
2017/0319846 A1*  11/2017  Plachta ................ A61N 1/0556
2018/0304071 A1*  10/2018  Mevel ................ A61N 1/36053
2019/0076650 A1*   3/2019  Befahy .............. A61N 1/36053

OTHER PUBLICATIONS

Sharif Khan et al. "Reliability of spring interconnects for high channel-count polyimide electrode arrays" Journal of Micromechanics & Microengineering, Institute of Physics Publishing, Bristol, GB, vol. 28, No. 5, Mar. 8, 2018 (Mar. 8, 2018), p. 55007, [retrieved on Mar. 8, 2018] DOI: 10.1088/1361-6439/AAAF2C ISSN: 0960-1317, XP020326536.

* cited by examiner

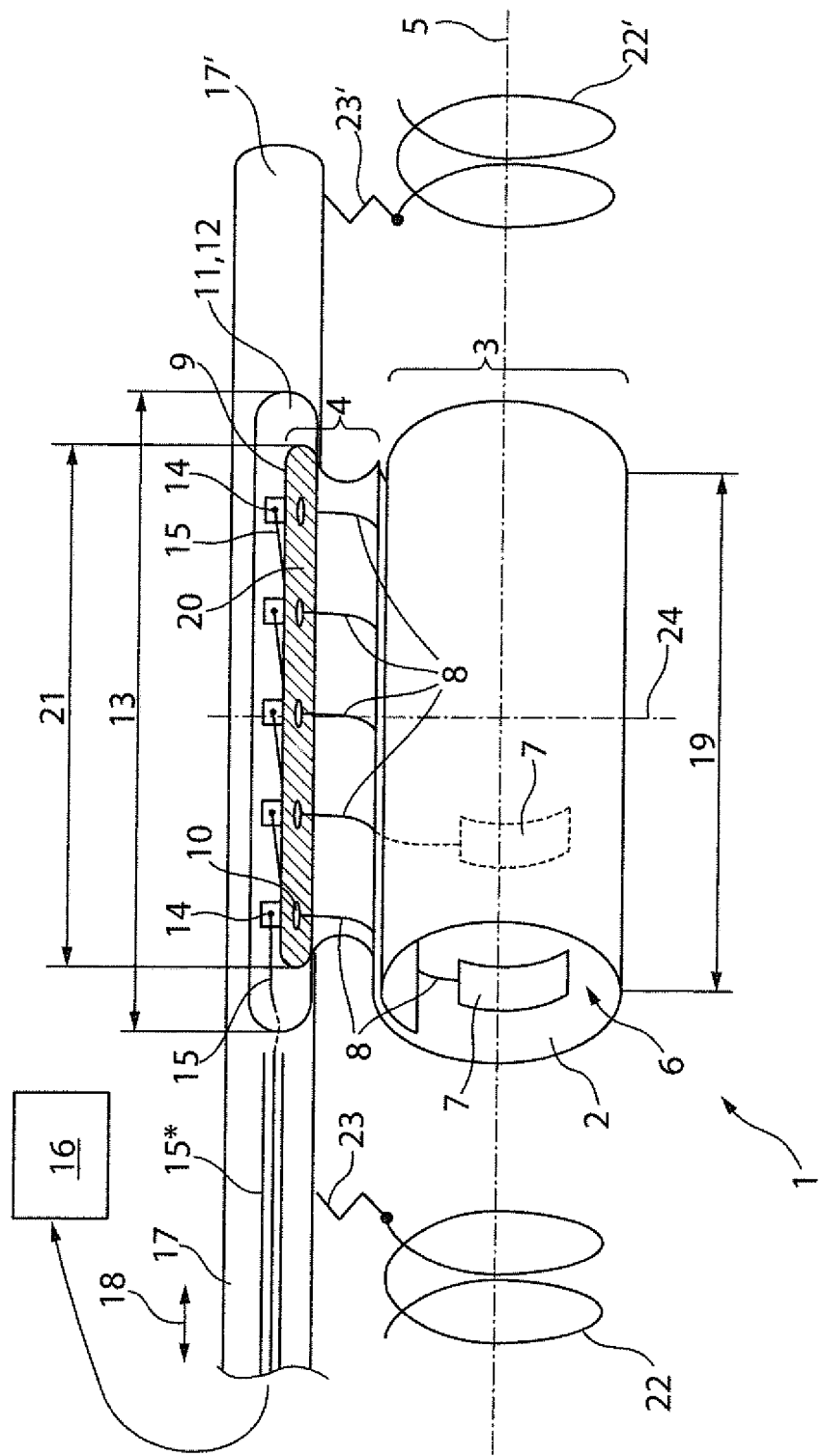

IMPLANT IN THE FORM OF A WOUND CUFF ELECTRODE ASSEMBLY

CROSS REFERENCE TO RELATED APPLICATIONS

Reference is made to PCT/EP2019/054643 filed Feb. 26, 2019, designating the United States, which claims priority to German Application No. 10 2018 204 036.2 filed Mar. 16, 2018, which are incorporated herein by reference in their entirety.

BACKGROUND OF THE INVENTION

Field of the Invention

The invention relates to a medical implant wound cuff electrode assembly. Extravasal or extra-neuronal fastening is used along an intracorporeal vessel or a nerve fiber bundle, having a flexible, biocompatible, film carrier substrate. A first region assumes a tube wound about a winding axis. The tube has a straight, cylindrical cavity which is radially delimited relative to the winding axis by a surface of the carrier substrate on which the at least one electrode surface is mounted. The surface is connected via at least one electrical line integrated within the carrier substrate to a non-flexible contact assembly.

Description of the Prior Art

Cuff electrodes of the aforementioned type are usually applied to record and also to apply electrical signals from intracorporeal vessels, in particular to nerve bundles. For this, cuff electrodes have a flexible, biocompatible carrier substrate, on the surface of which facing the nerve bundle at least one and preferably multiple electrodes are applied which have to be joined in intimate physical contact to the surface of a nerve bundle.

A cuff electrode of this type is disclosed in WO 2016/055512 A1. The carrier substrate of the cuff electrode comprises a polyimide film, which for the purpose of at least section-wise automatic winding about a winding axis, has undergone mechanical film pre-tensioning. Through the process of winding the cuff electrode about the nerve bundle, the individual electrodes of the cuff electrode come into direct surface contact with the epineurium of a nerve fiber bundle. By way of a force-applied form-fitting connection, the cuff electrode attaches itself to the nerve fiber bundle. The carrier substrate regions become overlapped through the rolling up or a winding process to lie on each other in a loosely sliding manner.

The electrical lines leading from the individual electrodes of the cuff electrode each extend, are electrically insulated within the polyimide film and end at a side edge area of the polyimide film which is spatially separated from the wound region of the cuff electrode. The ends of the electrical lines are each connected via an electrical contact assembly to electrical feed and discharge lines, via which the cuff electrode is connected to an implantable electrical supply, which is located intracorporeally to be separated from the cuff electrode.

Because of the natural sensitivity of nerve fibers to external mechanical influences, the mechanical loads acting on the nerve fiber bundle must be kept as low as possible. On the other hand it must be ensured that the cuff electrode surrounds the nerve fiber bundle stably enough to guarantee as durable and fixed joining of the cuff electrode along the nerve fiber bundle as possible.

Practical experience with the use of cuff electrodes shows, on the one hand, that through the loose winding of the carrier substrate, sometimes in multiple layers, around a nerve fiber bundle, a dynamic radial expansion of the cuff electrode is possible, through which the cuff electrode is able to adapt to natural changes in shape of the nerve fiber bundle, while on the other hand external forces acting on the cuff electrode can significantly deform its winding geometry through which the nerve fiber bundle can be exposed to considerable mechanical stresses which could lead to irreversible damage.

DE 44 33 111 A1 describes a cuff electrode comprising a flexible, multiple-layer substrate of non-conductive silicone on which there are raised electrodes made of conductive silicone. The conductor paths leading to the electrodes run between the non-conductive layers and are also made of conductive silicone. The setting of different pre-stresses in the multiple-layer structure of the cuff electrode brings about the rolled-up form of the cuff electrode.

SUMMARY OF THE INVENTION

The invention is a cuff electrode which has a flexible, biocompatible, film carrier substrate, which in a first region, through being wound about a winding axis, assumes the form of a tube which comprises a straight, cylindrical cavity. The cavity is delimited radially relative to the winding axis by a surface of the carrier substrate on which the at least one electrode surface is mounted, which is connected via at least one electrical line integrated within the carrier substrate to a non-flexible contact assembly on which the at least one electrical line is connected to at least one of an electrical feed and discharge line which leads to an implantable electrical supply unit formed separately from the implant by the simplest way to ensure that the cuff electrode exerts a force or pressure effect on the nerve fiber bundle which is as even and gentle as possible. This should apply in particular to those cases in which the cuff electrode is stressed by tensile forces acting along the electrical feed and discharge lines, caused by the body's own movements.

In accordance with the invention, the medical implant is a wound cuff electrode assembly characterised by the contact assembly being firmly joined to the carrier substrate along a dimensionally stable joining region. The joining region has a spatial length which is orientated in parallel to the winding axis, wherein the contact assembly in orthogonal projection relative to the winding axis overlaps the first region of the carrier substrate which is wound to form a tube.

The design of the cuff electrode of the invention, involves an application of the contact assembly relative to the carrier substrate region of the cuff electrode, which through a rolling up or winding process takes on the form of a tube and in the implanted state locally surrounds a nerve fiber bundle, which is based on experience gained with a known cuff electrode according to WO 2016/055512 A1. In the known cuff electrode, the region of the film carrier substrate which directly and in one piece adjoins the first region of the carrier substrate which is wound to form a tube, is essentially a band or strip. All electrical lines connected to the electrodes of the cuff electrode extend along the band-shaped carrier substrate region. The band carrier substrate region has a length essentially orientated in parallel to the winding axis and by way of an orthogonally formed, narrow band section is centrally locally connected to a carrier substrate region wound to form a tube. In the event of tensile or thrust forces acting along the band-like carrier substrate orientated in parallel to the winding axis, asymmetrical forces are exerted on the carrier substrate region wound to form the tube. Along the winding axis, on the one side of the wound carrier substrate, the resulting stress conditions can lead to tighter winding and associated constriction and on the opposite side of the wound carrier substrate region to expansion and associated local unwinding, through which the dwelling nerve bundle is subjected to significant heterogenic pressure or force effects.

The embodiment in accordance with the invention prevents such stress situations asymmetrically acting on the nerve bundle. The contact assembly which is made of a non-flexible material, for example a ceramic, acts as a force coupler, which transmits at least one of tensile and thrust forces acting along at least one of the electrical feed and discharge lines as evenly as possible to the carrier substrate region which is wound into a tube and is applied around a nerve fiber bundle in a mesh-like manner. Through this, an asymmetrical winding geometry in which one end of the tube acquires a small, and the other end a larger diameter, is also avoided. Preferably force transmission via the contact assembly to the carrier substrate region being wound into a tube takes place evenly along the entire axial length of the tube. In this way any shear forces acting on the nerve bundle can be avoided. Preferably the contact assembly and the carrier substrate are connected via a joining region that has a length orientated in parallel to the winding length which maximally corresponds to the mutual overlapping between the contact assembly and the tube in an orthogonal projection relative to the winding axis. Here it is particularly advantageous if the longitudinal extent of the contact assembly is equal to or greater than the tube length.

Examples of embodiments are also possible in which the dimensions of the longitudinal extension of the contact assembly, the tube length and the length of the joining region differ from each other. In these cases it must advantageously be ensured that the contact assembly is firmly joined relative to the carrier substrate so that the longitudinal extension of the contact assembly, the tube length and the length of the joining region each have a common central axis orthogonally orientated relative to the winding axis.

Preferably the contact assembly comprises a plate carrier on which the at least one electrical line on the cuff electrode side is in contact with an electrode applied to the carrier which preferably is by use of a microflex contact. The electrode on the carrier side is in turn connected to a further electrode surface, applied separately to the carrier, on which at least one of the electrical feed and discharge line leading to the separate supply unit is electrically connected by welding, soldering or a bonding connection. On the plate carrier there are multiples electrode/electrode surface pairs, via which a corresponding number of electric lines on the cuff electrode side are connected to corresponding to at least one of feed and discharge lines combined into one cable strand.

At least one of the electrical feed and discharge line or the feed and discharge lines which are combined into one cable strand as well the plate carrier, is surrounded by an elastic material, which in the joining region is connected to the carrier substrate in a fluid-tight manner. The elastic material which surrounds at least one of an electrical feed and discharge in a fluid-tight tube or matrix forms a strand having a longitudinal extension with a length determined in accordance with the intracorporeally separate positioning of the cuff electrode and the supply unit.

Compared to the carrier width, the plate carrier has a much larger dimensioned carrier length having a longitudinal extent which is orientated parallel to the winding axis. The comparatively narrow carrier shape is preferably dimensioned in such a way that it is embedded within the strand, along which the at least one of a feed and discharge line is integrated, without a substantial change in shape. A specific embodiment is explained below in more detail.

In a preferred embodiment, for the purpose of additional force distribution of the forces acting on the nerve fiber bundle via the cuff electrode, at least one additional fastening as a wound cuff or a helical structure is applied adjacent to the cuff electrode along the strand or tube containing at least one of the electrical feed and the discharge line. The additional fastening comprises, like the cuff electrode, a straight cylindrical cavity, which is aligned coaxially to the winding axis.

In a further preferred embodiment, in the longitudinal extension of the strand, the strand or tube can be a strand prolongation which adjoins the contact assembly and on which a second fastening of the type of the aforementioned first fastening is formed and applied. In this way at least one of the tensile and thrust forces acting along at least one of the feed and the discharge line can be deflected or transmitted symmetrically distributed in relation to the force-electrode assembly along the nerve bundle.

All electrical conductor structures applied on the carrier substrate, including the at least one electrode surface and the at least one electrical line electrically connected to the electrode surface are each produced in one piece, which is preferably a metal deposition process, so that there are no joining points and associated discontinuous electrical impedance differences along the electrical conductor structure.

BRIEF DESCRIPTION OF THE DRAWING

The invention will be described below without restricting the general inventive concept by way of an example of embodiment with reference to the drawing. In this:

FIG. 1 shows an example of embodiment of a medical implant designed in accordance with the invention.

DESCRIPTION OF THE INVENTION

FIG. 1 shows a cuff electrode 1 configured in a wound cuff electrode assembly with a film carrier substrate 2, which preferably is made of a polyimide film. The carrier substrate 2 comprises two regions 3, 4 connected in one piece. The first region 3 of the carrier substrate 2 is wound about a winding axis 5. This first region 3 of the carrier substrate 2, which is wound as a tube keeps its wound-up shape due to tensile forces inherent in the material which have been imparted through an appropriate treatment of the film carrier substrate 2. For example, by use of thermal treatment, a straight cylindrical cavity 6 is formed which is axially open at both sides. Applied on the surface, facing the straight cylindrical cavity 6, of the first region 3 of the carrier substrate 2 wound into a tube, is at least one electrode surface 7, and preferably multiple electrode surfaces. Each electrode surface is directly in physical contact with the outer wall of a nerve fiber bundle, which is not shown in more detail. Each of the electrode surfaces 7 is in one-piece contact with an electrical line 8. All surfaces 7 extend inside the carrier substrate 2 in an electrically insulated manner.

The second region 4 of the carrier substrate 2, which directly adjoins the first region 3 of the carrier substrate 2 in one piece, comprises a lateral edge 9, facing away from the first region 3, along which the electrical lines 8 end to be arranged next to each other and are each, via a microflex contact 10, in contact with an electrode applied on the contact assembly 11. The contact assembly 11 is configured as a plate carrier 12, preferably comprising a ceramic plate which has a longitudinal extension 13. The length of the carrier 12 is much greater than its width.

The electrodes applied on the plate carrier 12 connect each of the electrical leads 8 to an electrical contact surface 14, which is on the upper side of the plate carrier 12, on which is a soldered, bonded or welded connection. At least one of an electrical feed and discharge line 15 is in contact and according to FIG. 1 extends to the left laterally to the contact assembly 11. All of the feed and discharge lines 15 are connected to the respective contact surface 14 combined into a cable strand 15* which extends to supply unit 16 which is formed separately from the cuff electrode 1. Cable streamed provides, for example, control signals as well as electrical energy for operating the cuff electrode 1. The wire feed and discharge lines 15 are combined into cable strand 15* and are connected to the supply unit 16 via a fluid-tight plug connection (not shown) for a separate manipulation of the supply unit 16, as for example replacement. For electrical insulation, as well as for protection against the moist intracorporeal environment, the cable strand 15*, comprising all the at least one electrical feed and discharge lines 15, is surrounded by a silicone tube 17 or embedded in a silicone strand 17.

In order to ensure that tensile or thrust forces 18 acting along the silicone strand 17 are distributed as evenly as possible along the entire length 19 of the first region 3 of the carrier substrate 2 wound into the tube. The joining region 20, between the contact assembly 11 and the second region 4 of the carrier substrate 2, is joined by way of a firm joint connection to the surface of the plate carrier 12 of the contact assembly 11 and is positioned in orthogonal projection relative to the winding axis 5 at least partially, and preferably completely, as shown in FIG. 1 to overlap relative to the axial extension 19 of the area 3 of the carrier substrate 2 wound into a tube. Irrespective of the actual dimensions of the respective lengths of the contact assembly 11, the joining region 20 and first region 3 of the carrier substrate 2 wound into the tube, the longitudinal extension (13) of the contact assembly (11), the tube length (19) and the joining region length (21) preferably have a common middle axis (24) orientated orthogonally relative to the winding axis (5).

In FIG. 1, the joining region 20 has a longitudinal extension 21 which approximately corresponds with the length 19 of the region 3 of the carrier substrate 2 wound into form the tube. In this case, force transmission by the contact assembly 11 onto the carrier substrate 2 takes place via the joining region 20 evenly over the entire length 19.

Optionally, a fastening 22, 22' can be provided along the winding axis 5 unilaterally relative to the cuff electrode 1 or bilaterally relative to the cuff electrode 1, which like the cuff electrode 1 can nestle around the outer circumference of a nerve bundle under the exertion of force. The fastening 22, 22' can be a wound cuff or a known helical structure, preferably made of a silicone material. The left fastening 22 in FIG. 1 is applied directly to the silicone strand 17 by a connection 23. The connection 23 is preferably in designed as a one-piece bonded connection to the fastening 22 and the connection 23 as well as the silicone strand 17 are produced from the same material as part of a uniform manufacturing process. The connection 23 can be configured to be a seamless transition between the silicone strand 17 and fastening 22 up to a unique joining geometry in the form of a rectilinear, zig-zag, spiral or helical connection arm. There is also optionally provided fastening 22' on the right side of the cuff electrode 1 which is applied on a strand prolongation 17. In this case too, the connection 23' can be the same as described above.

LIST OF REFERENCES

1 Cuff electrode
2 Carrier substrate
3 First region of the carrier substrate
4 Second region of the carrier substrate
5 Winding axis
6 Straight cylinder cavity
7 Electrode surface
8 Electrical line
9 Connection end edge of the carrier substrate
10 Microflex contact
11 Contact assembly
12 Plate-like carrier
13 Longitudinal extension of the contact assembly
14 Electrode surface
15 Electrical feed and/or discharge
15* Cable strand
16 Supply
17 Silicone strand
17' Strand prolongation
18 Thrust-tensile forces
19 Length of the second region 3 of the carrier substrate wound to form a tube
20 Joining region
21 Length of the joining region
22, 22' Fastening
23, 23' Connection
25 Middle axis

The invention claimed is:

1. A medical implant configured as a wound cuff electrode comprising:
a flexible, biocompatible, film with a first region, which is wound about a winding axis to form a straight, cylindrical cavity limited radially relative to the winding axis including at least one electrode surface, at least one electrical line integrated within the film which is connected to a non-flexible contact to which the at least one electrical line is connected to at least one of an electrical feed and discharge line at a joining region for connection when implanted to an implantable electrical supply separated from the implant;
a contact assembly including a longitudinal extension orientated parallel to the winding axis and joined to the film along the joining region having an area with a length orientated in parallel to the winding axis and the contact assembly projecting orthogonally relative to the winding axis to overlap a first region of a carrier substrate;
the contact assembly includes a plate carrier on which the at least one electrical line contacts an electrical contact to which at least one of the electrical feed line and the discharge line are electrically connected; and
at least one of the electrical feed line and the discharge line together with the plate carrier are surrounded by an elastic material in the joining region to provide a fluid tight connection.

2. The medical implant according to claim 1, wherein the contact assembly is configured relative to the carrier substrate to have a longitudinal extension of the contact assembly and a length of the first region of the carrier substrate overlaps to form a projection extending orthogonally from winding axis.

3. The medical implant according to claim 2, wherein:
the joining region between the contact assembly and an implantable control assembly is longitudinally orientated parallel to the winding axis which has a maximum mutual overlap with the longitudinal orientation of the contact assembly relative to the winding axis.

4. The medical implant according to claim 3, wherein the contact assembly is joined to the film so that the contact assembly, a tube and the joining region have a common axis orientated orthogonally to the winding axis.

5. The medical implant according to claim 2, wherein the contact assembly is joined to the film so that the contact assembly, a tube and the joining region have a common axis orientated orthogonally to the winding axis.

6. The medical implant according to claim 2, wherein the first region of the film has at least one winding around the winding axis at least one region in which the carrier substrate moveably overlaps itself radially relative to the winding axis.

7. The medical implant according to claim 1, wherein:
the joining region between the contact assembly and an implantable control assembly is longitudinally orientated parallel to the winding axis which has a maximum mutual overlap with the longitudinal orientation of the contact assembly relative to the winding axis.

8. The medical implant according to claim 7, wherein the contact assembly is joined to the film so that the contact assembly, a tube and the joining region have a common axis orientated orthogonally to the winding axis.

9. The medical implant according to claim 7, wherein the film includes a second region adjoining the first region which includes a side edge laterally limiting the film on which the at least one electrical line is electrically connected to the contact of the joining region.

10. The medical implant according to claim 7, wherein the first region of the film has at least one winding around the winding axis at least one region in which the carrier substrate moveably overlaps itself radially relative to the winding axis.

11. The medical implant according to claim 1, wherein the contact assembly joined to the carrier substrate has a common axis orientated orthogonally to the winding axis.

12. The medical implant according to claim 11, wherein the film includes a second region adjoining the first region which includes a side edge laterally limiting the film on which the at least one electrical line is electrically connected to the contact of the joining region.

13. The medical implant according to claim 1, wherein the film includes a second region adjoins the first region which includes a side edge laterally limiting the film on which the at least one electrical line is electrically connected to the contact of the joining region.

14. The medical implant according to claim 1, wherein the elastic material surrounding at least one of the at least one electrical feed and the discharge line is a strand including a longitudinal extension adjoining the contact assembly, is parallel to the winding axis, and includes a region of the strand containing at least one of the electrical feed and discharge line, a first fastener comprising a straight cylindrical cavity having a wound cuff or a helix with the straight cylindrical cavity being coaxial to the winding axis.

15. The medical implant according to claim 14, wherein the longitudinal extension of the strand includes an extension opposite to the contact assembly which includes a second fastener.

16. The medical implant according to claim 1, wherein the first region of the film has at least one winding around the winding axis at least one region in which the carrier substrate moveably overlaps itself radially relative to the winding axis.

* * * * *